United States Patent
Perrin et al.

(10) Patent No.: US 9,913,713 B2
(45) Date of Patent: Mar. 13, 2018

(54) INTRALARYNGEAL PROSTHESIS

(71) Applicant: Protip Medical, Strasbourg (FR)

(72) Inventors: Nicolas Perrin, Schiltigheim (FR); Maurice Berenger, Savasse (FR)

(73) Assignee: PROTIP MEDICAL (FR)

( * ) Notice: Subject to any disclaimer, the term of this patent is extended or adjusted under 35 U.S.C. 154(b) by 30 days.

(21) Appl. No.: 14/916,811

(22) PCT Filed: Sep. 5, 2014

(86) PCT No.: PCT/EP2014/068913
§ 371 (c)(1),
(2) Date: Mar. 4, 2016

(87) PCT Pub. No.: WO2015/032886
PCT Pub. Date: Mar. 12, 2015

(65) Prior Publication Data
US 2016/0228239 A1    Aug. 11, 2016

(30) Foreign Application Priority Data

Sep. 5, 2013  (FR) ..................... 13 58530

(51) Int. Cl.
*A61F 2/20*  (2006.01)

(52) U.S. Cl.
CPC ............... *A61F 2/203* (2013.01); *A61F 2/20* (2013.01); *A61F 2230/0069* (2013.01);
(Continued)

(58) Field of Classification Search
CPC ....... A61F 2/20; A61F 2/203; A61F 2002/206
See application file for complete search history.

(56) References Cited

U.S. PATENT DOCUMENTS

| 2,198,241 | A | 4/1940 | Brehm |
| 4,374,669 | A | 2/1983 | Mac Gregor |

(Continued)

FOREIGN PATENT DOCUMENTS

| DE | 1791014 A1 | 10/1971 |
| DE | 202004010382 U1 | 11/2004 |

(Continued)

OTHER PUBLICATIONS

International search report dated Jun. 13, 2013 for PCT/EP2013/073117.

(Continued)

*Primary Examiner* — Thomas J Sweet
*Assistant Examiner* — Daniel Bissing
(74) *Attorney, Agent, or Firm* — Wilson Sonsini Goodrich & Rosati

(57) ABSTRACT

The invention relates to an intralaryngeal prosthesis which is not at risk of getting blocked and which allows the patient to breathe comfortably. For this purpose, the prosthesis comprises a tubular body pierced by a proximal opening and a convex dome-shaped valve (10), the valve being arranged such that: the distal end (15) of the valve forms a rim (16) which covers a portion of the tubular body (2), and such that a space (17) exists between the distal end (15) of the valve and the tubular body (2) such that air can enter the proximal opening (8) of the tubular body through said space (17).

12 Claims, 4 Drawing Sheets

(52) U.S. Cl.
CPC ............... *A61F 2230/0071* (2013.01); *A61F 2250/0018* (2013.01); *A61F 2250/0071* (2013.01)

(56) References Cited

U.S. PATENT DOCUMENTS

| | | | |
|---|---|---|---|
| 4,435,853 A | 3/1984 | Blom et al. | |
| 4,538,607 A | 9/1985 | Saul | |
| 4,550,448 A | 11/1985 | Kenna | |
| 4,911,716 A | 3/1990 | Blom et al. | |
| 5,358,522 A | 10/1994 | Montgomery et al. | |
| 5,391,205 A | 2/1995 | Knight | |
| 5,507,809 A | 4/1996 | Blom | |
| 5,765,560 A | 6/1998 | Verkerke et al. | |
| 5,855,612 A | 1/1999 | Ohthuki et al. | |
| 5,911,756 A * | 6/1999 | Debry .............. | A61F 2/203 623/9 |
| 5,957,978 A | 9/1999 | Blom | |
| 6,159,008 A | 12/2000 | Kumar | |
| 6,193,751 B1 | 2/2001 | Singer | |
| 6,358,222 B1 | 3/2002 | Grundei | |
| 6,402,515 B1 | 6/2002 | Patti et al. | |
| 6,565,581 B1 | 5/2003 | Spence et al. | |
| 6,666,208 B1 | 12/2003 | Schumacher et al. | |
| 6,913,623 B1 | 7/2005 | Zhu | |
| 7,025,784 B1 | 4/2006 | Blom | |
| 7,166,128 B1 | 1/2007 | Persson | |
| 7,998,200 B2 | 8/2011 | Nelson | |
| 8,167,936 B2 | 5/2012 | Kurian | |
| 8,551,168 B2 | 10/2013 | Debry et al. | |
| 8,603,388 B2 | 12/2013 | Debry et al. | |
| 8,800,564 B2 | 8/2014 | Scott | |
| 9,364,313 B2 | 6/2016 | Perrin et al. | |
| 2002/0156527 A1 | 10/2002 | Persson | |
| 2002/0193879 A1 | 12/2002 | Seder et al. | |
| 2005/0025656 A1 | 2/2005 | Bhaduri et al. | |
| 2005/0171602 A1 | 8/2005 | Goldberg et al. | |
| 2006/0276893 A1 | 12/2006 | Nelson | |
| 2008/0027473 A1 | 1/2008 | Bjerken | |
| 2008/0050452 A1 | 2/2008 | Chen et al. | |
| 2008/0072912 A1 | 3/2008 | Scott | |
| 2009/0026660 A1 * | 1/2009 | Nelson .............. | A61F 2/203 264/331.13 |
| 2009/0043386 A1 | 2/2009 | Persson | |
| 2009/0253099 A1 | 10/2009 | Debry et al. | |
| 2010/0227294 A1 | 9/2010 | Takagi | |
| 2011/0106251 A1 | 5/2011 | Debry et al. | |
| 2011/0264214 A1 | 10/2011 | Nelson | |
| 2012/0215306 A1 | 8/2012 | Fagan et al. | |
| 2013/0072759 A1 | 3/2013 | Li | |
| 2014/0288648 A1 | 9/2014 | Walder et al. | |
| 2014/0303745 A1 | 10/2014 | Anderson | |
| 2015/0094809 A1 | 4/2015 | Perrin et al. | |
| 2015/0238659 A1 | 8/2015 | Dove et al. | |
| 2015/0305860 A1 | 10/2015 | Wang et al. | |

FOREIGN PATENT DOCUMENTS

| | | |
|---|---|---|
| DE | 202007000655 U1 | 3/2007 |
| EP | 0651980 A2 | 5/1995 |
| EP | 0815807 A1 | 1/1998 |
| EP | 0856299 A1 | 8/1998 |
| EP | 1736119 A2 | 12/2006 |
| EP | 1937185 B1 | 2/2010 |
| EP | 1940480 B1 | 6/2010 |
| EP | 2240120 B1 | 7/2012 |
| FR | 1102694 A1 | 10/1955 |
| FR | 1211841 A | 3/1960 |
| FR | 2559067 A1 | 8/1985 |
| FR | 2891133 A1 | 3/2007 |
| FR | 2924331 A1 | 6/2009 |
| FR | 2979534 A1 | 3/2013 |
| JP | H 01275766 A | 11/1989 |
| WO | WO 94/19045 A1 | 9/1994 |
| WO | WO 96/35399 A1 | 11/1996 |
| WO | WO 02/066693 A1 | 8/2002 |
| WO | WO 02/083031 A2 | 10/2002 |
| WO | WO 2004/060438 A2 | 7/2004 |
| WO | WO 2005/097001 A1 | 10/2005 |
| WO | WO 2005/102458 A2 | 11/2005 |
| WO | WO 2007/034077 A1 | 3/2007 |
| WO | WO 2007/048935 A2 | 5/2007 |
| WO | WO 2007/051177 A2 | 5/2007 |
| WO | WO 2009/098408 A2 | 8/2009 |
| WO | WO 2011/051177 A1 | 5/2011 |
| WO | WO 2013/034858 A1 | 3/2013 |
| WO | WO 2013/079362 A2 | 6/2013 |

OTHER PUBLICATIONS

International search report dated Dec. 17, 2012 for PCT/FR2012/051996.

Notice of allowance dated Feb. 18, 2016 for U.S. Appl. No. 14/361,136.

Office action dated Jun. 16, 2015 for U.S. Appl. No. 14/343,321.

Office action dated Aug. 28, 2015 for U.S. Appl. No. 14/361,136.

Office action dated Nov. 24, 2015 for U.S. Appl. No. 14/343,321.

* cited by examiner

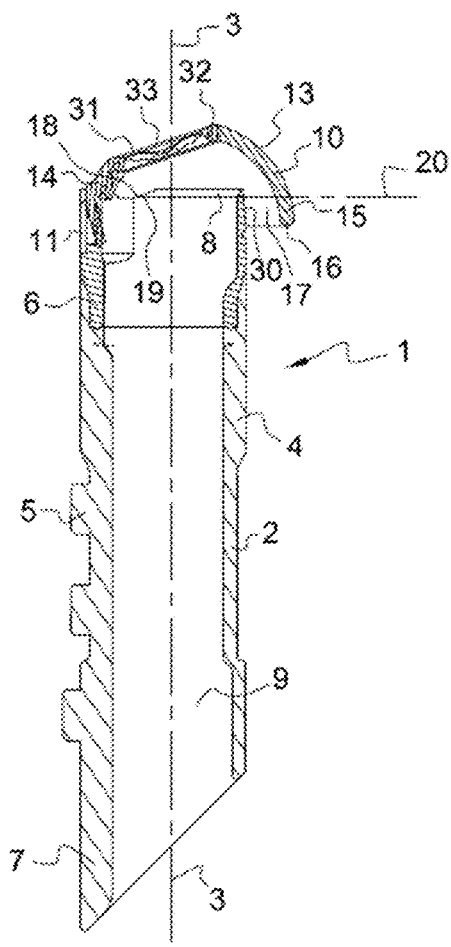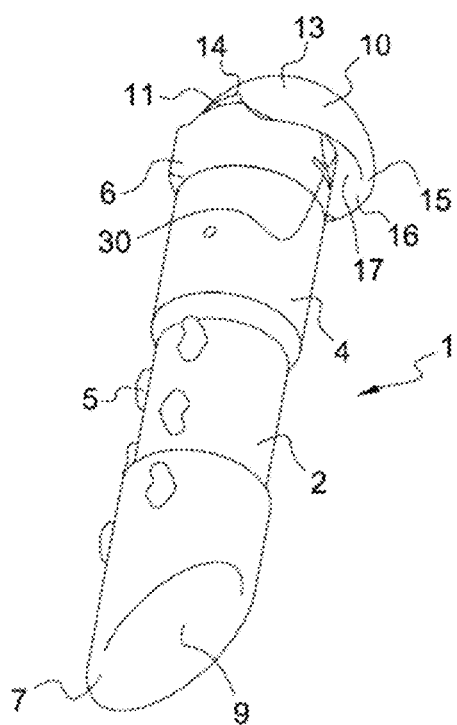
Fig. 1
Fig. 2

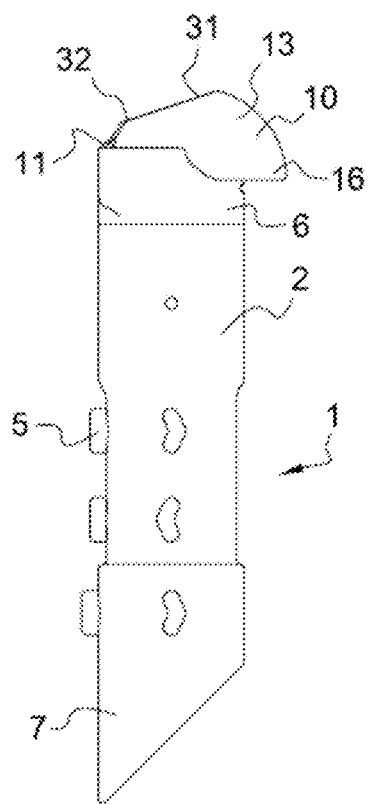
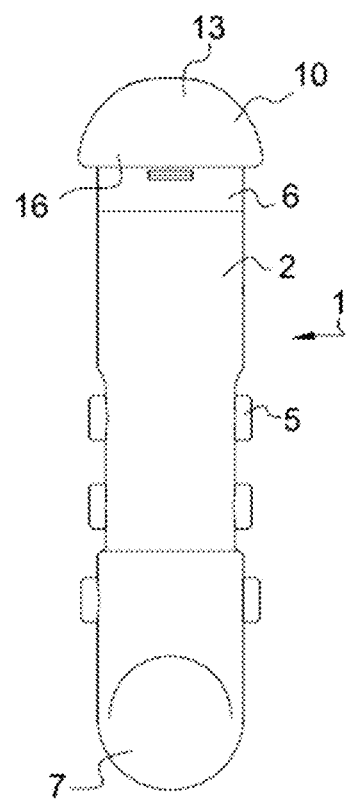
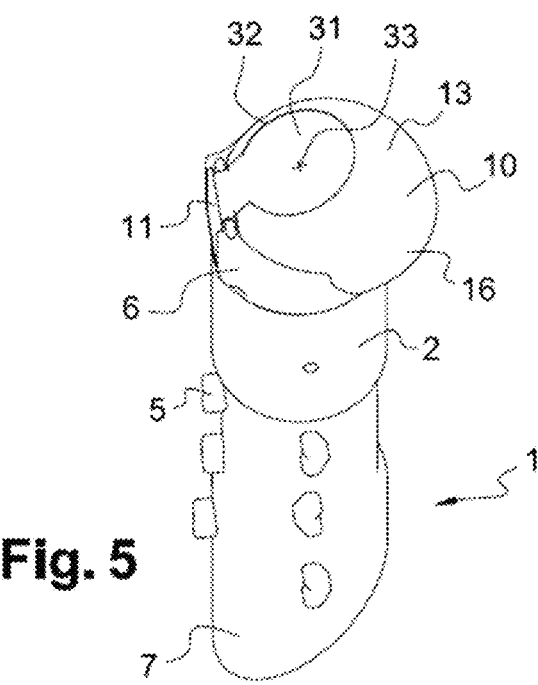
Fig. 3
Fig. 4
Fig. 5

INTRALARYNGEAL PROSTHESIS

TECHNICAL FIELD

The present invention relates to an intralaryngeal prosthesis.

PRIOR ART

The main function of the larynx is to close the airways during swallowing, in order to protect them and to prevent a food bolus from entering them instead of passing through the esophagus. This closure is effected by a neuromuscular reflex closing the glottis, resulting from the adduction of muscle groups arranged at three levels (aryepiglottic fold, ventricular bands and vocal cords). In case of dysfunction at one of these levels, problems arise that affect swallowing, since the larynx can no longer ensure correct closure of the airways, such that the food bolus can enter the airways.

To overcome this problem, the document EP 0 815 807 describes an intralaryngeal prosthesis by which a dysfunction of the larynx can be overcome. For this purpose, the intralaryngeal prosthesis has a tubular body which is intended to be inserted into the larynx of a patient. The tubular body has one of its ends beveled. A closure valve, which is aligned with the beveled end of the tubular body, is secured to this end. The closure valve is able to prevent elements from passing into the tubular body. To allow air to pass despite this into the tubular body, the beveled end is pierced by orifices which have substantially a crenellated shape and connect the interior and the exterior of said tubular body. However, these orifices have a tendency to be blocked by saliva or by the food bolus, which impairs the patient's breathing.

DISCLOSURE OF TRE INVENTION

The invention aims to overcome the disadvantages of the prior art by making available an intralaryngeal prosthesis which prevents the passage of the food bolus and of saliva into the airways, which does not become blocked, and which allows the patient to breathe easily.

To do this, a first aspect of the invention relates to an intralaryngeal prosthesis designed to be introduced into a larynx, the prosthesis having:
- a tubular body having a proximal end surrounding a proximal opening;
- a valve having a proximal end and a distal end;
- a hinge connecting the proximal end of the valve to the proximal end of the tubular body in such a way that the valve can be placed in a normal position (at rest), in which it covers the proximal opening, or in an open position, in which it does not cover the proximal opening;
- the valve being arranged in such a way that, in the normal position:
- the distal end of the valve forms a rim which covers a part of the tubular body, and that
- a space exists between the distal end of the valve and the tubular body, in such a way that air can enter the proximal opening of the tubular body through this space.

Thus, the orifices allowing the air to circulate in the tubular body are no longer formed by crenellations made in the tubular body but instead by a space in the form of a chicane provided between the valve and the tubular body. In addition, the fact that the valve forms an edge covering a part of the tubular body ensures that saliva and the food bolus evacuated from the surface of the valve are not evacuated into the tubular body. However, in order to allow air to circulate despite this, the valve is configured in such a way that a space exists between the valve, more precisely the rim thereof, and the tubular body. The air can thus enter the tubular body through this space, without saliva or the food bolus entering the tubular body on account of the rim.

The intralaryngeal prosthesis can likewise have one or more of the following features either independently or in all the possible technical combinations.

Advantageously, the valve has a convex dome shape, by which it is possible to avoid the stagnation of the food bolus and of saliva on the valve, since these elements are evacuated by gravity.

However, other geometries of the valve are conceivable, in particular wherein the valve is flat (it could then be beveled with respect to the tubular body, that is to say the plane of the valve is not perpendicular to the axis of the tubular body). The other geometries of the valve must be determined in such a way that they make it possible to avoid the stagnation of the food bolus or the saliva on the valve, which have to slide by gravity into the esophagus.

The tubular body preferably extends, at least in part, along a reference axis so as to be able to be inserted into the larynx of a patient.

In a particular embodiment, the tubular body has two zones:
- a first zone (I) (for example cylindrical) extending along a reference axis (this zone being intended to be inserted wholly or partly into the larynx of a patient, or the end of a tracheal ring as described in the application WO 2013/079362)
- a second zone (II) (including the proximal end) with external dimensions smaller than the external dimensions of the first zone (in such a way that one passes from the first zone to the second zone via a narrowing of the external dimensions of the tubular body). Generally, the internal lumen (cross section, proximal opening (8)) of the second zone is smaller than the internal lumen defined in the first zone. This second zone can have a frustoconical shape or a beveled shape (or the shape of the nozzle of a whistle or the mouthpiece of a recorder).

If the first zone (I) is generally of revolution about an axis, the second zone (II) does not necessarily have an axis of symmetry.

The principle of implementation of this embodiment makes it possible to use a valve having the same diameter as the first cylindrical zone of the tubular body, while at the same time maintaining the space between the proximal part of the tubular body and said valve.

In fact, in order to maintain the space between the valve and the tubular body, the dimensions of the valve are greater than those of the proximal end of said tubular body. However, it is not possible to reduce too far the dimensions of the part of the tubular body intended to be inserted into the larynx of the patient so that the patient is able to breathe without obstruction and without effort. In some cases, the use of a valve of a larger size (diameter) than that of the tubular body can cause an obstruction after implantation in the patient.

Thus, the use of a tubular body as described above, of which the proximal end is of a smaller dimension than the distal dimensions of said tubular body, thus makes it possible to reduce the size of the valve and use a valve with a diameter equal to that of the distal end of the tubular body, while at the same time maintaining the space existing between the proximal part of the tubular body and the rim of said valve covering it.

The fact that the valve forms a rim which covers a part of the tubular body and that a space exists between this part of the tubular body and the rim can be achieved in different ways.

Provision can in particular be made that a valve is offset with respect to the tubular body in such a way that:
the distal end of the valve forms a rim which covers a part of the tubular body and that
a space exists between the distal end of the valve and the tubular body in such a way that air can enter the proximal opening of the tubular body through this space.

The valve is preferably offset in a direction away from the hinge.

Provision can likewise be made that the valve has transverse dimensions greater than those of the tubular body in such a way that:
the distal end of the valve forms a rim which covers a part of the tubular body and that
a space exists between the distal end of the valve and the tubular body in such a way that air can enter the proximal opening of the tubular body through this space.

Of course, both of the preceding embodiments can be implemented separately or combined.

According to one embodiment, the valve has a seal (cap) with weakened zones, the seal being able to be pierced by an intubation probe. Thus, the valve can be pierced easily and quickly in case of emergency intubation. The seal preferably has a receiving zone adapted such that an intubation probe can be placed in this receiving zone without risk of slipping on the upper face of the valve.

Advantageously, the valve has a lower face, the hinge being elastically deformable in such a way as to allow the valve to move to the open position when a force greater than a threshold force is exerted on the lower face of the valve. Thus, during expectoration, coughing or deep exhalation, or when the surgeon wishes to check the airways with the aid of an endoscope for example, the hinge allows the valve to open upward.

Advantageously, the valve has a lower face, the hinge being elastically deformable in such a way as to bring the valve back to the normal position when no force greater than a threshold force is exerted on the lower face of the valve. Thus, during normal breathing, the valve remains in the normal position and thus covers the proximal opening of the tubular body in order to protect it.

According to a preferred embodiment, the valve has an upper face, the upper face of the valve being treated, at least in part, by an anti-adhesive treatment. The anti-adhesive treatment is able to strengthen the effect of the shape of the valve in preventing the stagnation of the food bolus and of the saliva on the valve. This anti-adhesive treatment can be provided, for example, by polishing or shot-peening the upper face of the valve or by an anti-adhesive layer deposited on the valve.

The proximal end of the tubular body can likewise be conditioned by surface treatment.

Advantageously, the valve has centering means arranged on its lower face, the proximal end of the tubular body having complementary centering means, the centering means of the valve being designed to cooperate with the complementary means of the tubular body so as to guide the valve and ensure that it returns to the desired position when it moves from the open position to the normal position. For this purpose, the centering means can be formed by a centering truncated cone protruding from the lower face of the valve. The complementary centering means can in this case be formed by a frustoconical orifice provided in a transverse wall of the tubular body, the orifice being able to receive the centering cone.

This technical solution ensures that the valve returns to the neutral position.

Advantageously, the tubular body has an elastically deformable central part, which allows the intralaryngeal prosthesis to be inserted into the larynx of a patient easily and without surgical intervention.

The central part of the tubular body is preferably made of silicone.

The proximal end of the tubular body is preferably made of titanium in order to facilitate the attachment of the hinge on the tubular body and to avoid the deformations of the proximal end when the hinge deforms.

Advantageously, the valve is made of titanium so as to be sufficiently rigid that it does not deform under the effect of the food bolus or the saliva.

Advantageously, the valve is elliptic so as to better adapt to the anatomy of the patient.

Advantageously, the hinge is made of silicone, but it can also be made of any other biocompatible elastic material. As is described below, the hinge has a restoring force which is sufficient to allow the valve to cover the proximal opening when it is at rest but to open when a force greater than a threshold force is applied to the lower face of the valve.

All of the materials used to produce the intralaryngeal prosthesis are biocompatible.

According to different embodiments, the tubular body can be flexible, semi-rigid or even rigid.

Advantageously, said tubular body has external protruding stubs, allowing said prosthesis to be fixed in position inside the larynx, by means of said stubs bearing against the inner wall thereof.

Advantageously, in order to allow said prosthesis to sit easily at the level of the vocal cords, the distal end of said tubular body, opposite the proximal end, has a smaller diameter than at the proximal end or than the central part of the tubular body.

Advantageously, the distal end is beveled.

BRIEF DESCRIPTION OF THE FIGURES

Other features and advantages of the invention will become clear on reading the following detailed description in which reference is made to the attached figures, in which:

FIG. 1 shows a sectional view of an intralaryngeal prosthesis according to an embodiment of the invention;

FIG. 2 shows a perspective view of the intralaryngeal prosthesis from FIG. 1;

FIG. 3 shows a side view of the prosthesis from FIG. 1;

FIG. 4 shows a front view of the prosthesis from FIG. 1;

FIG. 5 shows a top view of the prosthesis from FIG. 1;

Figure 6:
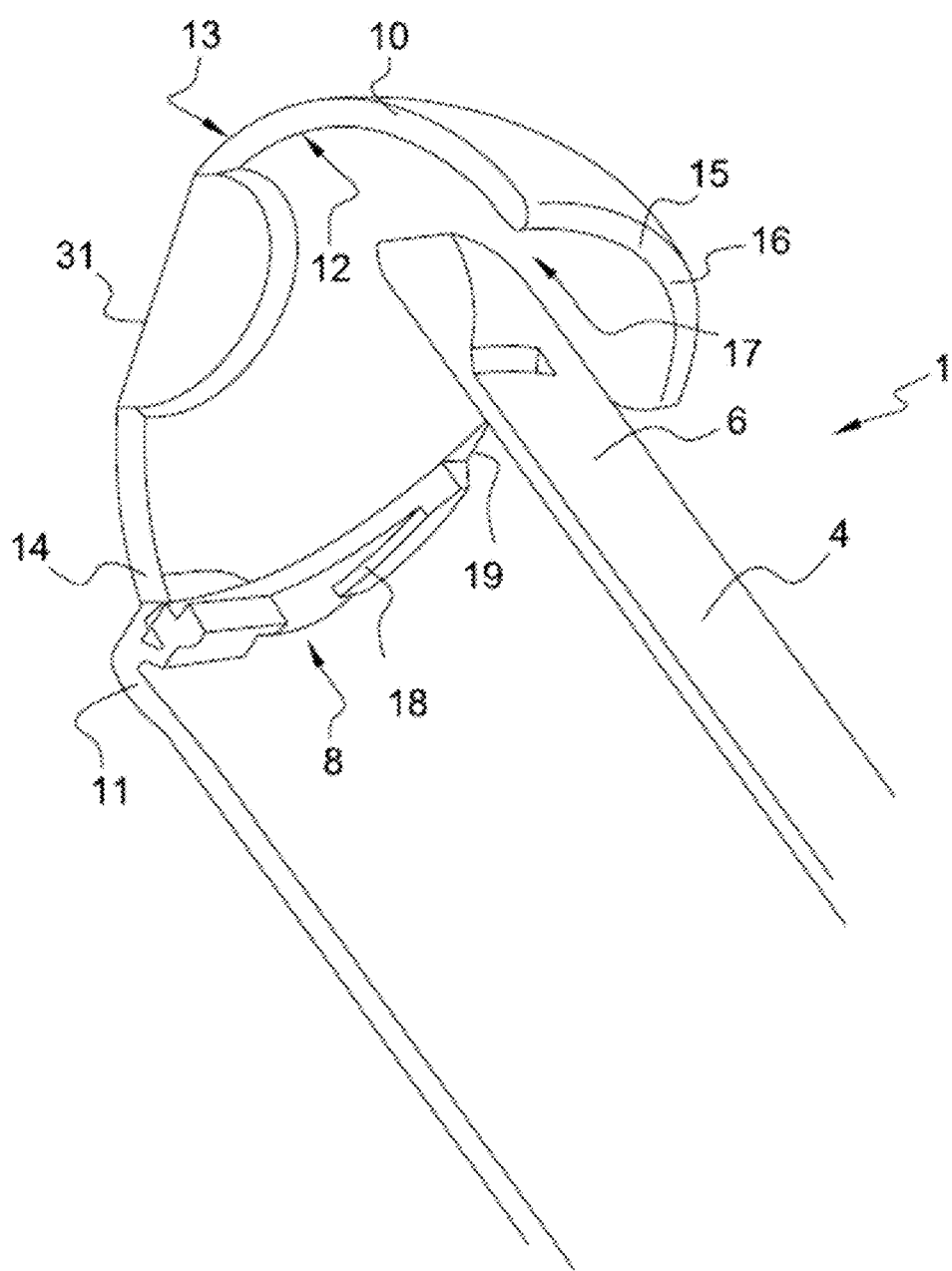
FIG. 6 shows an enlarged view of the interior of the prosthesis from FIG. 1.
Figure 7:
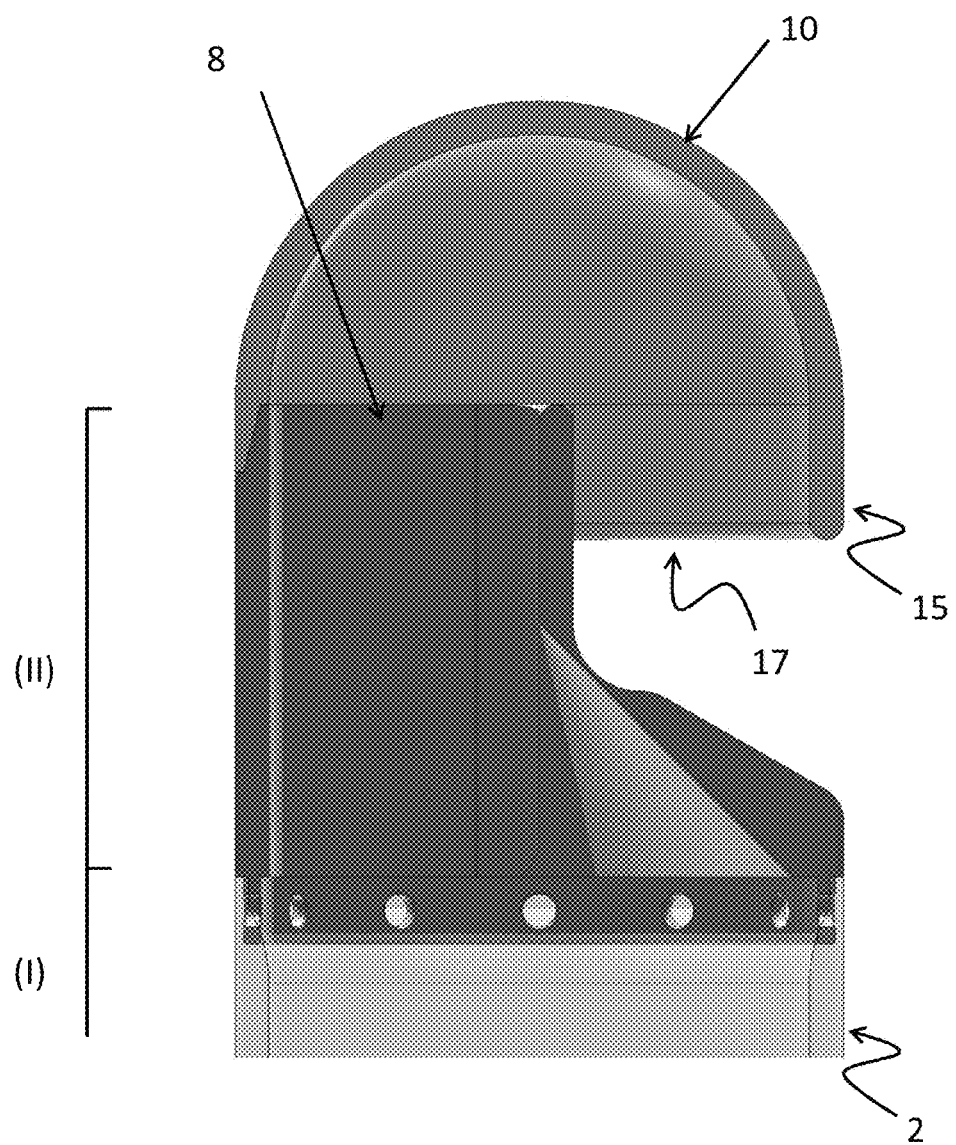
FIG. 7 shows a sectional view of the zone (I) containing the proximal opening (8) of the tubular body (2), in the shape of a mouthpiece of a recorder, and a small part of the zone (I) of the tubular body (2), and the valve (10), of which the diameter is identical to that of the cylindrical zone (I) of the tubular body (2). This figure shows the valve (10) in the rest position. It also shows the space (17) between the distal end

(15) of the valve (10) and the tubular body, allowing the air to circulate and allowing the patient to breathe.

For greater clarity, elements that are identical or similar are labeled by identical reference signs in all of the figures.

DETAILED DESCRIPTION OF AT LEAST ONE EMBODIMENT

With reference to the figures, the intralaryngeal prosthesis 1 has a tubular body 2. The tubular body 2 extends along a reference axis 3. The tubular body 2 has a tubular shape along the reference axis. The tubular body 2 preferably has a central part 4. The central part 4 is preferably elastically deformable. For this purpose, the central part 4 is preferably made of silicone. The intralaryngeal prosthesis can thus be easily inserted via the mouth and without a surgical intervention in the larynx of a patient. The central part 4 can be provided with roughened areas 5 in such a way as to make it easier to hold in place in the larynx of the patient. The prosthesis can be fitted in place without a tracheotomy.

In the case where the tubular body contains a zone (I) and a zone (II) as described above, the central part is present in zone (I).

The tubular body 2 likewise has a proximal end 6 and a distal end 7. The proximal end 6 and distal end 7 are thus opposite each other. The distal end 7 is preferably beveled. The proximal end 6 is preferably rigid, in such a way as to be stronger, to allow the fastening of a hinge and to allow the valve to return to position on the tubular body. The rigid proximal end 6 likewise permits the attachment of the ancillary device for fitting the intralaryngeal prosthesis in place. The proximal end 6 is preferably made of titanium.

The proximal end 6 is pierced by a proximal opening 8. The proximal opening 8 leads into a cylindrical opening 9, which passes right through the tubular body 2.

The intralaryngeal prosthesis 1 preferably has a valve 10. The valve 10 can be placed in a normal position, in which it covers the proximal opening 8, and an open position, in which it does not cover the proximal opening 8. The valve 10 is preferably made of titanium. The valve 10 has a lower face 12 and an upper face 13. The lower face 12 of the valve is directed toward the tubular body. The upper face 13 of the valve is directed away from the tubular body. The valve 10 has a proximal end 14 and a distal end 15.

The lower face 12 of the valve is preferably provided with centering means 18 arranged to engage in complementary centering means 19 of the tubular body 2 in such a way as to ensure the correct positioning of the valve when it moves from the open position to the normal position. These centering means 18 can, for example, comprise a centering cone, while the complementary centering means 19 comprise a complementary conical orifice.

The valve 10 is connected to the tubular body 2 by a hinge 11, which is elastically deformable to allow the valve to move from the normal position to the open position, and vice versa. In other words, the hinge is flexible and can bend. More precisely, the proximal end 14 of the valve is connected to the hinge 11. The hinge 11 is preferably made of silicone. The hinge 11 is configured in such a way as to allow the valve to move to the open position when a force greater than a threshold force is applied to the lower face 12 of the valve 10. Thus, in the event of expectoration, the valve opens to facilitate the exhalation by the patient. This is also the case in the event of coughing or sneezing. The surgeon is also able to open the valve in order to check the airways, for example by endoscope. Moreover, the hinge 11 is designed to bring the valve 10 back to the normal position when no force greater than the threshold force is applied to the lower face 12 of the valve. Thus, the valve 10 is always brought back to the normal position in such a way as to protect the proximal opening 8, except in the case of a force greater than the threshold force. During normal breathing, the valve 10 is thus in the normal position.

In order to prevent the passage of saliva and/or of a food bolus into the proximal opening 8 of the tubular body, while allowing air to pass through this opening, the intralaryngeal prosthesis has the features set forth in detail below.

The valve 10 preferably has a dome shape. More precisely, the valve 10 preferably has a convex shape and a concavity directed toward the tubular body 2. Thus, under the effect of gravity, the food bolus settling on the valve would be evacuated. The dome shape thus makes it possible to avoid the stagnation of the food bolus and of the saliva on the valve. In addition, in order to heighten this effect, an anti-adhesive covering can be provided on the upper surface 13 of the valve.

In this embodiment, the valve has a symmetry of revolution. However, it would also be possible to have a valve with an elliptical cross section, having the longer axis parallel to a transverse axis 20 connecting the proximal end of the valve to its distal end, or a longer axis perpendicular to such a transverse axis 20.

In addition, the valve 10 is arranged in such a way that:
- the distal end 15 of the valve forms a rim 16 which covers a part 30 of the tubular body 2, and that
- a space 17 exists between the distal end 15 of the valve 10 and the tubular body 2, in such a way that air can enter the proximal opening 8 of the tubular body 2 through this space 17.

For this purpose, provision can in particular be made that the valve has transverse dimensions greater than the transverse dimensions of the tubular body 2. In this document, "transverse dimensions" designates a dimension considered perpendicularly with respect to the reference axis 3 of the tubular body.

According to another embodiment, provision can be made that the valve 10 is offset with respect to the tubular body, in such a way that the valve 10 is offset in the direction away from the hinge 11. Of course, these two embodiments can be used independently of each other or in combination.

The space 17 and the space between the lower face 12 of the valve and the wall transverse to the distal end 6 form a S-shaped baffle, which allows the air to enter the proximal opening 8 while ensuring that food or saliva cannot enter the proximal opening 8.

The rim 16 is preferably cut in such a way as to match the tubular body 2 along the longitudinal direction, on either side of the space 17.

Moreover, the valve 10 can be provided with a seal 31 with weakened zones 32, such that the seal can be pierced by an intubation probe in the event of emergency intubation. The seal 31 is preferably made of silicone. The seal 31 is preferably overmolded on the valve 10 at the same time as the hinge 11, which is also preferably overmolded on the valve 10. The valve 10, preferably made of titanium, is provided with through-holes which are placed on the periphery of the seal and are able to ensure the mechanical stability of the seal 31 on the valve 10. The seal 31 is hermetic unless torn, and it is strong enough not to be breached by food or saliva. For example, the seal 31 can be made in the following way. In a first step, the seal 31 made of silicone is overmolded on the valve 10. In a second step, a tool equipped with blades is able to notch the center of the seal 31, preferably in a cross shape or spider shape. These notches do not pass all the way through; a fine thickness of silicone thus makes it possible to join together parts of the seal. Leak-tightness is thus maintained between the top and bottom of the valve. This technical solution will make it possible, once pierced by an intubation probe, to keep the petals of the seal connected to the valve. According to different embodiments, the seal can be flat, as is shown in FIGS. 1 and 4, or convex. Moreover, the seal can have a receiving zone 33 capable of receiving the end of a probe, in such a way as to prevent the end of the probe from sliding on the seal. For this purpose, the receiving zone preferably forms a concave cross with its concavity directed away from the tubular body 2. In other words, the concavity of the receiving zone 33 is preferably counter to the concavity of the valve 10. The receiving zone 33 is preferably aligned with the reference axis 3 of the tubular body 2, in such a way as to begin guiding an intubation probe in the axis of the tubular body. Consequently, when the valve is offset with respect to the tubular body, the receiving zone is offset with respect to the valve.

Of course, the invention is not limited to the embodiments described with reference to the figures, and variants could be envisioned without departing from the scope of the invention. The valve could in particular have a shape other than the dome shape; for example, it could be triangular or trapezoidal.

The invention claimed is:

1. An intralaryngeal prosthesis comprising:
   a tubular body (2) having a proximal end (6) surrounding a proximal opening (8);
   a valve (10) having a proximal end (14) and a distal end (15);
   a hinge (11) connecting the proximal end (14) of the valve (10) to the proximal end (6) of the tubular body (2) said hinge being configured to allow selective placement of the valve (10) in a normal position, in which it covers the proximal opening (8), or in an open position, in which it does not cover the proximal opening (8);
   wherein the valve (10) is configured such that, in the normal position:
   the distal end (15) of the valve forms a rim (16) which covers a part of the tubular body (2), and the distal end (15) of the rim (16) extends distally from the proximal opening (8) of the tubular body to form a space (17) between the distal end (15) of the valve and the tubular body (2), in such a way that air can enter the proximal opening (8) of the tubular body through this space (17).

2. The intralaryngeal prosthesis as in claim 1, wherein the valve (10) has a convex dome shape.

3. The intralaryngeal prosthesis as in claim 1, wherein the tubular body (2) extends along a reference axis (3), the valve (10) being offset with respect to the tubular body (2) in a direction away from the hinge (11).

4. The intralaryngeal prosthesis as in claim 1, wherein the tubular body (2) extends along a reference axis (3), the valve (10) having transverse dimensions greater than those of the tubular body.

5. The intralaryngeal prosthesis as in claim 1, wherein the tubular body has a first zone (I) extending along a reference axis, and a second zone (II) having external dimensions smaller than the external dimensions of the first zone.

6. The intralaryngeal prosthesis as in claim 1, wherein the second zone has a frustoconical shape, a beveled shape, the shape of the nozzle of a whistle, or the shape of the mouthpiece of a recorder.

7. The intralaryngeal prosthesis as in claim 1, wherein the valve (10) has a seal with weakened zones, the seal being able to be pierced by an intubation probe.

8. The intralaryngeal prosthesis as in claim 7, in which the seal has a receiving zone capable of receiving the end of an intubation probe.

9. The intralaryngeal prosthesis as in claim 1, wherein the valve (10) has a lower face (12), the hinge (11) being elastically deformable in such a way as to allow the valve (10) to move to the open position when a force greater than a threshold force is exerted on the lower face (12) of the valve (10).

10. The intralaryngeal prosthesis as in claim 1, wherein the valve (10) has a lower face (12), the hinge (11) being elastically deformable in such a way as to bring the valve (10) back to the normal position when no force greater than a threshold force is exerted on the lower face (12) of the valve (10).

11. The intralaryngeal prosthesis as in claim 1, wherein the valve (10) has an upper face (13), the upper face (13) of the valve (10) being treated, at least in part, by an anti-adhesive treatment.

12. The intralaryngeal prosthesis as in claim 1, wherein the tubular body (2) has an elastically deformable central part (4).

* * * * *